US008735103B2

(12) United States Patent
Chung et al.

(10) Patent No.: US 8,735,103 B2
(45) Date of Patent: May 27, 2014

(54) NATURAL CONVECTION-DRIVEN PCR APPARATUS AND METHOD USING DISPOSABLE POLYMER CHIP

(75) Inventors: Kwang-Hyo Chung, Daejon (KR); Dae-Sik Lee, Daejon (KR); Hyeon-Bong Pyo, Daejon (KR); Seon-Hee Park, Daejon (KR)

(73) Assignee: Electronics and Telecommunications Research Institute, Daejon (KR)

( * ) Notice: Subject to any disclaimer, the term of this patent is extended or adjusted under 35 U.S.C. 154(b) by 1158 days.

(21) Appl. No.: 11/866,979

(22) Filed: Oct. 3, 2007

(65) Prior Publication Data

US 2008/0131956 A1 Jun. 5, 2008

(30) Foreign Application Priority Data

Dec. 5, 2006 (KR) .................. 10-2006-0122492
Jun. 1, 2007 (KR) .................. 10-2007-0053800

(51) Int. Cl.
*C12P 19/62* (2006.01)
*C12M 1/36* (2006.01)
*C12M 1/38* (2006.01)
*C12Q 1/68* (2006.01)
*B01L 7/00* (2006.01)

(52) U.S. Cl.
CPC .............. *C12Q 1/686* (2013.01); *C12Q 1/6844* (2013.01); *B01L 7/52* (2013.01)
USPC ..................... 435/91.2; 435/286.5; 435/287.2

(58) Field of Classification Search
CPC ...... C12Q 1/686; C12Q 1/6844; C12Q 1/689; C12Q 1/6853; C12Q 1/6848; C12Q 1/6883; C12Q 1/6827; C12Q 1/6816; C12Q 2600/156; C12Q 1/6869; C12Q 1/6886; A61K 2300/00; A61K 2039/505; A01J 5/10

USPC ................. 435/91.2, 286.5, 287.2; 422/110
See application file for complete search history.

(56) References Cited

U.S. PATENT DOCUMENTS 6,586,233 B2   7/2003  Benett et al.
2004/0028566 A1*  2/2004  Ko et al. .............. 422/100

(Continued)

FOREIGN PATENT DOCUMENTS

KR   2003-0024592 A   3/2003
KR   2006-0025027     3/2006
SU   EP 0504435 A1 *  9/1992  .......... C12Q 1/68

OTHER PUBLICATIONS

Zongyuan Chen, et al., "Thermosiphon-Based PCR Reactor: Experiment and Modeling," Analytical Chemistry, vol. 76, No. 13, pp. 3707-3715, Jul. 1, 2004.

(Continued)

*Primary Examiner* — Michael Hobbs
(74) *Attorney, Agent, or Firm* — Rabin & Berdo, P.C.

(57) ABSTRACT

Provided is a natural convection-driven polymerase chain reaction (PCR) apparatus and method, which can periodically change temperature of a sample to make a natural convection-driven flow in a loop-shaped channel on a disposable polymer chip and contacting heating metal members maintained at different temperatures with channels. The natural convection-driven PCR apparatus includes: a polymer chip having a plurality of channels connected together to form a loop-shaped microchannel, a sample being filled inside the channels; a plurality of heating metal members contacting the loop-shaped microchannel of the polymer chip and transferring heat; a temperature controller connected to the heating metal members to maintain the heating metal members at different temperatures; a plurality of heaters connected to the heating metal members and the temperature controller to supply heat to the heating metal members; and temperature sensors connected to the heating metal members and the temperature controller.

16 Claims, 10 Drawing Sheets

(56) References Cited

U.S. PATENT DOCUMENTS

| | | |
|---|---|---|
| 2004/0043479 A1* | 3/2004 | Briscoe et al. ............. 435/288.5 |
| 2004/0152122 A1 | 8/2004 | Hwang et al. |
| 2006/0280629 A1* | 12/2006 | Chang et al. ............... 417/413.3 |
| 2007/0004032 A1* | 1/2007 | Lee et al. ................... 435/288.5 |
| 2008/0161553 A1* | 7/2008 | Ohnishi et al. ................ 536/127 |
| 2008/0176292 A1* | 7/2008 | Ugaz et al. ................... 435/91.2 |

OTHER PUBLICATIONS

Zhang et al., "PCR microfluidic devices for DNA amplification", Science direct, Biotechnology Advances, vol. 24 (3), pp. 243-284, 2006.

* cited by examiner

NATURAL CONVECTION-DRIVEN PCR APPARATUS AND METHOD USING DISPOSABLE POLYMER CHIP

CROSS-REFERENCE(S) TO RELATED APPLICATIONS

The present invention claims priority of Korean Patent Application Nos. 10-2006-0122492 and 10-2007-0053800, filed on Dec. 5, 2006, and Jun. 1, 2007, respectively, which are incorporated herein by reference.

BACKGROUND OF THE INVENTION

1. Field of the Invention

The present invention relates to a natural convection-driven polymerase chain reaction (PCR) apparatus and method using a disposable polymer chip; and, more particularly, to a natural convection-driven PCR apparatus and method, which can periodically change the temperature of a sample to make a natural convection-driven flow in a loop-shaped channel by forming the loop-shaped channel on a disposable polymer chip and contacting heating metal members maintained at different temperatures with channels.

2. Description of Related Art

Generally, biochip, biosensor, and chemical sensor for biochemical analysis are required to make a reaction by applying a temperature change to a sample. For the temperature charge, a variety of heating methods have been proposed. A typical device for making a reaction by applying a temperature change to a sample is a deoxyribonucleic acid (DNA) amplification device that amplifies DNA by adding an enzyme to a DNA template and applying a predetermined temperature cycling.

More specifically, the temperature cycling is to change a temperature to two or three different degrees. That is, the temperature cycling changes a temperature to different degrees in order for a denaturation step for separating a DNA double helix, an annealing step for controlling the DNA template to find a complementary pair, and an extension step for growing the DNA. The DNA amplification due to the temperature change is referred to as a polymer chain reaction (PCR).

The heating methods for changing the PCR temperature may be classified into two categories. The first method is to change a temperature of a sample by externally applying a temperature change to a sample filled and stopped in a chamber. The second method is to change a temperature of a sample by moving the sample to an environment having a desired temperature condition. The first method does not require an additional fluid control because the sample is stopped. However, a lot of time is taken to change the external temperature environment when a thermal capacity of the external environment is large. In addition, a control operation for the temperature change is additionally required. Thus, the first method becomes complicated.

The second method can rapidly and accurately change the temperature of the sample because the external temperature environment can be constantly monitored. However, the second method requires a fluid control operation for moving the sample.

To overcome the disadvantages of the two methods, a method for periodically applying a temperature change to a sample has been proposed. This method uses a natural convection to rapidly and accurately change the temperature of the sample by passing the sample through a constant temperature zone, without additional external fluid control operation.

The natural convection is a flow phenomenon derived from the generation of a buoyant force when the density of a fluid placed under a gravitational field is changed due to heat. The fluid flows downward in a relatively cold external environment and flows upward in a relative hot external environment. In the PCR, although there is a difference according to kinds of the DNA sample, which is an amplification target, the denaturation step is performed in a temperature range from 90° C. to 97° C., the annealing step is performed in a temperature range from 50° C. to 65° C., and the extension step is performed in a temperature range from 68° C. to 74° C. Using the temperature difference, the natural convection flow may be generated.

Since this flow is naturally generated at any place where the gravitational field exists, the external fluid control operation for moving the sample may be omitted. The known PCR apparatus and method using the natural convection will be described below.

Examples of the PCR using the natural convection are disclosed in U.S. Pat. No. 6,586,233, entitled "Convectively Driven PCR Thermal-Cycling", U.S. Patent Application Publication No. 2004/0152122, entitled "Method And Apparatus for Amplification of Nucleic Acid Sequences by Using Thermal Convection", and U.S. Patent Application Publication No. 2006/0216725, entitled "Polymer Chain Reaction Apparatus Using Marangoni Convection And Polymer Chain Reaction Method Using The Same." In U.S. Pat. No. 6,586,233, trenches for thermal isolation are installed and a pouch for containing a sample is inserted into a heating block heated to two different temperatures. The PCR temperature cycling is achieved using the convection generated when the sample is clamped.

In U.S. Patent Application Publication No. 2004/0152122, a relatively high temperature region is located lower in height than a relatively low temperature region, thereby forming a spatial temperature distribution. The convection is generated by spatially changing a temperature of a sample using the spatial temperature distribution. In U.S. Patent Application Publication No. 2006/0216725, both sidewalls of a chamber are maintained at a constant temperature and Marangoni convection is used. The Marangoni convection is generated by a surface tension gradient resulting from a temperature difference in an interface between a sample and air.

A paper entitled "Thermosiphon-Based PCR Reactor: Experiment and Modeling", Analytical Chemistry, Vol. 76, No. 13, Jul. 1, 2004, discloses a PCR method that constantly maintains temperatures of three aluminum heating blocks and forms a loop using a tube.

The conventional PCR apparatuses and methods disclosed in the above-described documents and paper uses the pouch-shaped sample container or tube, have the spatial temperature distribution, and generate the natural convection by applying the temperature change. In the case of using the pouch or tube, there is an inconvenience in placing the sample and the tube must be replaced when it is reused. Thus, mass-production is difficult. In addition, the conventional PCR apparatus has difficulty in effectively eliminating thermal interference using the spatial temperature change. Further, temperature interference may occur because the sidewall of the sample is locally heated and the sample does not change to a desired temperature in each temperature zone.

SUMMARY OF THE INVENTION

An embodiment of the present invention is directed to providing a natural convection-driven PCR apparatus and method using a disposable polymer chip, which can periodically change a temperature of a sample to make a natural convection-driven flow in the loop-shaped channel by forming a loop-shaped channel on the polymer chip and contacting heating metal members maintained at different temperatures with channels.

In addition, since the polymer substrate is used, mass production can be possible. The portability of the PCR apparatus can be improved because the simple temperature control is required instead of additional flow control. Since the polymer chip is fabricated in a microchannel type, the sample flows smoothly and the accurate temperature change of the sample can be achieved, thereby minimizing the interference between the samples. The sample can be fully filled inside the loop-shaped microchannel due to only the capillary flow without any air layer and thus the samples can move smoothly.

In accordance with an aspect of the present invention, there is provided a natural convection-driven polymerase chain reaction (PCR) apparatus using a disposable polymer chip, which includes: a polymer chip having a plurality of channels connected together to form a loop-shaped microchannel, a sample being filled inside the channels; a plurality of heating metal members contacting the loop-shaped microchannel of the polymer chip and transferring heat; a temperature controller connected to the heating metal members to maintain the heating metal members at different temperatures; a plurality of heaters connected to the heating metal members and the temperature controller to supply heat to the heating metal members; and temperature sensors connected to the heating metal members and the temperature controller.

The loop-shaped microchannel may include: an inlet through which the sample is introduced; a plurality of channels; a connection channel connecting the channels and through which the sample flows; and an outlet through which the sample is discharged.

The loop-shaped microchannel may further include a capillary stop valve for filling the channels with the sample without air layer.

The channels may include a denaturation channel, an annealing channel, and an extension channel.

The polymer chip may be formed by attaching a polymer film to a passage substrate having the channels formed using an injection molding or a hot embossing.

The passage substrate and the polymer film may be attached using a lamination process or an adhesive.

Surfaces of the channels of the polymer chip may be processed biologically, chemically and optically, thereby preventing biological molecule components in the heated fluid from being adsorbed onto the surfaces of the channels.

The heating metal member may include: a heating metal block connected to the heater to transfer heat generated from the heater; a heating metal pin protruding from the heating metal block to transfer heat generated from the heating metal block; and a heating metal contact block having one side protruding from the heating metal pin and contacting the channel of the polymer chip.

The heating metal block, the heating metal pin, and the heating metal contact block may be integrated such that the heating metal member is formed in a multiple slot shape, whereby a plurality of polymer chips are inserted thereinto.

The heating metal block is maintained at a constant temperature by the heater, the temperature controller, and the temperature sensors, and the sample inside the loop-shaped microchannel is heated to a constant temperature by the heating metal block, while the natural convection is generated by the heating, such that the sample flows along the loop and the temperature changes sequentially changes.

The heating metal member may further include a plurality of insulating members for minimizing thermal interference between the heating metal blocks maintained at different temperatures, the heating metal block being fixed between the insulating members.

The heater may be one among a film heater, a ceramic heater, and a rod heater.

The polymer chip may be inclined at a predetermined angle with respect to a gravitational field to control a natural convection-driven PCR time.

The natural convection-driven PCR apparatus may further include a fluorescent detector for obtaining PCR result in real time using the polymer chip.

The polymer chip may be formed of a material selected from the group consisting of polymethylmethacrylate (PMMA), polycarbonate (PC), cycloolefin copolymer (CC), polyamide (PA), polyethylene (PE), polypropylene (PP), polyphenylene ether (PPE), polystyrene (PS), polyoxymethylene (POM), polyetheretherketone (PEEK), polytetrafluoroethylene (PTFE), polyvinylchloride (PVC), polyvinylidene fluoride (PVDF), polybutyleneterephthalate (PBT), fluorinated ethylenepropylene (FEP), perfluoralkoxyalkane (PFA), and combination thereof.

A natural convection-driven PCR method using a natural convection-driven PCR apparatus employing a disposable polymer chip, wherein the PCR apparatus includes a polymer chip having a plurality of channels connected together to form a loop-shaped microchannel, a sample being filled inside the channels; a plurality of heating metal members contacting the loop-shaped microchannel of the polymer chip and transferring heat; a temperature controller connected to the heating metal members to maintain the heating metal members at different temperatures; a plurality of heaters connected to the heating metal members and the temperature controller to supply heat to the heating metal members; and temperature sensors connected to the heating metal members and the temperature controller, the natural convection-driven PCR method which includes: a) maintaining the heating metal member at a constant temperature using the heater, the temperature controller, and the temperature sensors; b) heating the sample placed in the channel to a predetermined temperature by contacting the heating metal member with the polymer chip in which a loop-shaped microchannel channel; b) generating the natural convection due to the heating; and c) sequentially changing the temperature of the sample by moving the sample along the loop due to the natural convection.

In addition, since the polymer substrate is used, low-cost mass production can be possible. The portability of the PCR apparatus can be improved because the simple temperature control is required instead of additional flow control.

Since the polymer chip is fabricated in a microchannel type, the sample flows smoothly and the interference or resistance is small. The sample can be fully filled inside the loop-shaped microchannel due to only the capillary flow without any air layer and thus the samples can move smoothly.

Further, the loop-shaped microchannel is formed in the polymer substrate that can be mass-produced, and the thermal interference of the heating metal member can be prevented, thereby achieving the accurate temperature change of the sample Furthermore, the loop-shaped microchannel of the polymer substrate is fully filled with the sample due to only the capillary flow without any air layer, thereby obtaining the smooth sample flow.

Moreover, the polymer chip can be easily integrated with various sensors that can be formed on a plane using a two-dimensional polymer substrate. The thermal interference is minimized because only the loop-shaped microchannel of the polymer chip is locally heated along the double-sided contacts. Since the very simple temperature control is required, the natural convection-driven PCR apparatus is small-sized, lightweight and easy to carry.

Other objects and advantages of the present invention can be understood by the following description, and become apparent with reference to the embodiments of the present invention. Also, it is obvious to those skilled in the art to which the present invention pertains that the objects and advantages of the present invention can be realized by the means as claimed and combinations thereof.

DESCRIPTION OF SPECIFIC EMBODIMENTS

The advantages, features and aspects of the invention will become apparent from the following description of the embodiments with reference to the accompanying drawings, which is set forth hereinafter.

Figure 1:
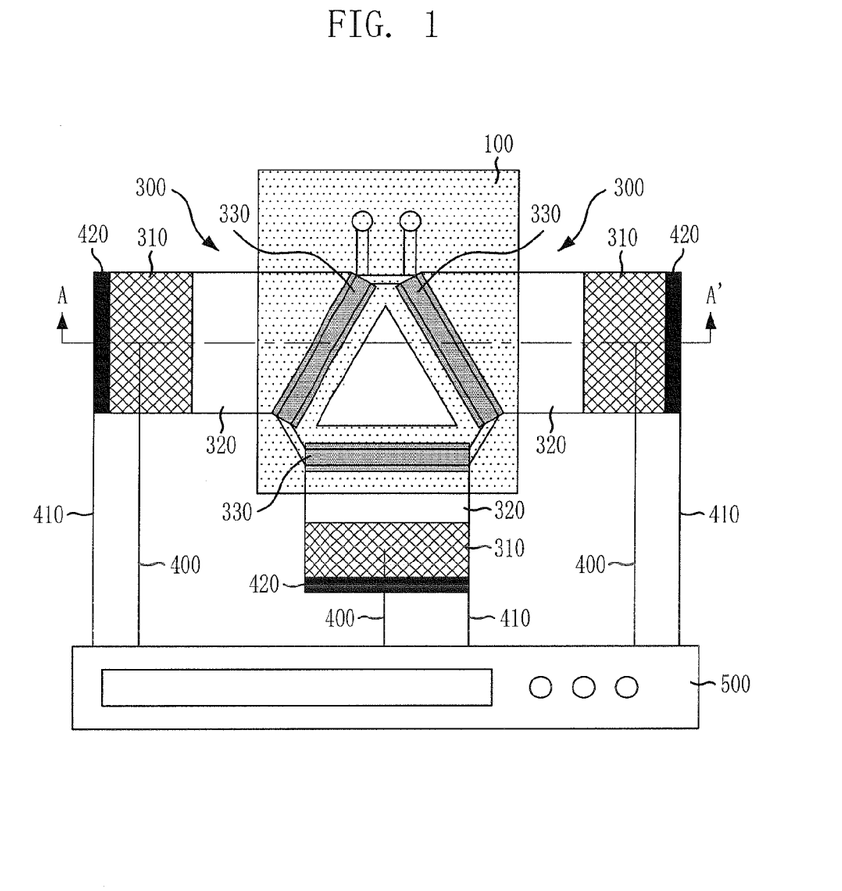
FIG. 1 illustrates a natural convection-driven PCR apparatus using a disposable polymer chip in accordance with an embodiment of the present invention.
Figure 2:
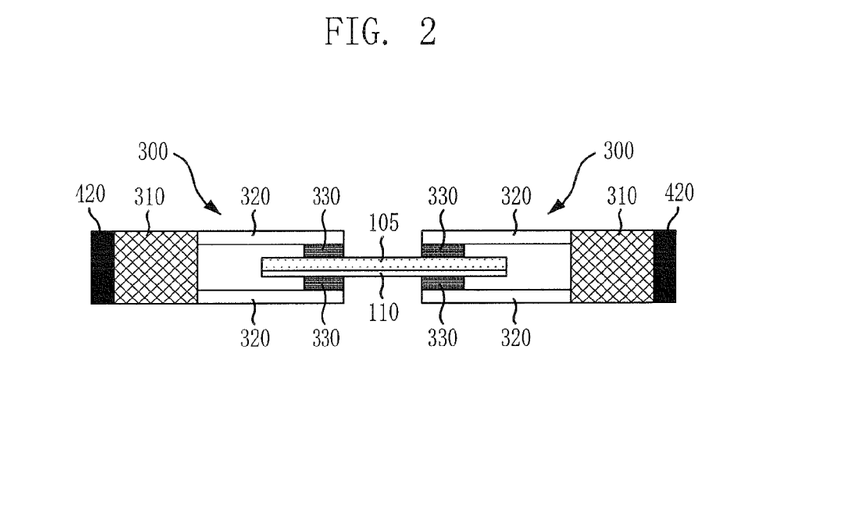
FIG. 2 is a sectional view taken along line A-A' of FIG. 1.

FIG. 1 illustrates a natural convection-driven PCR apparatus using a disposable polymer chip in accordance with an embodiment of the present invention, and FIG. 2 is a sectional view taken along line A-A' of FIG. 1. Referring to FIGS. 1 and 2, the natural convection-driven PCR apparatus includes a polymer chip 100, a plurality of heating metal members 300, a temperature controller 500, a heater 420, and temperature sensors 400.

The polymer chip 100 includes a passage substrate 105 and a polymer chip cover 110. A loop microchannel 200 (see FIGS. 3 and 5) in which a plurality of channels are connected is formed in the passage substrate 105.

The heating metal members 300 contact the loop microchannel 200 of the polymer chip and transfer heat. Each of the heating metal members 300 includes a heating metal block 310, a heating metal pin 320, and a heating metal contact block 330. The heating metal block 310 transfers heat from the heater 420 to the channel. The heating metal pin 320 is connected to the heating metal block 310 and is formed of a metal having high heat conductivity so as to easily transfer the heat of the heating metal block 310 to the channel. The heating metal contact block 330 protrudes from the heating metal pin 320. The heating metal contact block 330 contacts outer surfaces of the channels 210, 220 and 230 of the polymer chip 100, and transfers the heat of the heating metal block 310 to the channels of the polymer chip 100.

As described above, the heating metal block 310, the heating metal pin 320, and the heating metal contact block 330 of the heating metal member 300 may be integrated in a slot shape, so that the polymer chip 100 can be inserted.

The heating metal pins 320 are connected to the heating metal blocks 310 to form a plurality of slots, so that a lot of polymer chips can be mounted. In addition, the heating metal block 310 may be fixed and installed between insulating members so as to minimize thermal interference between the metal heating blocks maintained at different temperatures.

The contact surfaces of the heating metal contact blocks 310 contacting the channels of the polymer chip 100 are smoothly processed so that no air layer is formed and the heat can be easily transferred.

The temperature controller 500 maintains the heating metal blocks 310 at different temperatures, i.e., PCR temperatures, through the heater 420 and the temperature sensor 400.

The heaters 420 heat the heating metal blocks 310. The heaters 420 are connected or inserted into the heating metal blocks 310 and are connected to the temperature controller 500 through heater lines 410. Examples of the heaters 420 may include a film heater, a ceramic heater, and a rod heater.

The temperature sensors 400 detect temperatures of the heating metal blocks and are connected to the heating metal blocks 310 and the temperature controller 500.

As illustrated in FIG. 2, the polymer chip 100 is mounted in the slot-shaped space defined by the heating metal block 310, the heating metal pin 310, and the heating metal contact block 330, and the thermal interference can be prevented because of the spatial separation between the heating metal pins. In addition, since only the heating metal contact block 330 contacts the polymer chip 100, the interference between the different temperature zones on the polymer chip 100 can be minimized.

Figure 3:
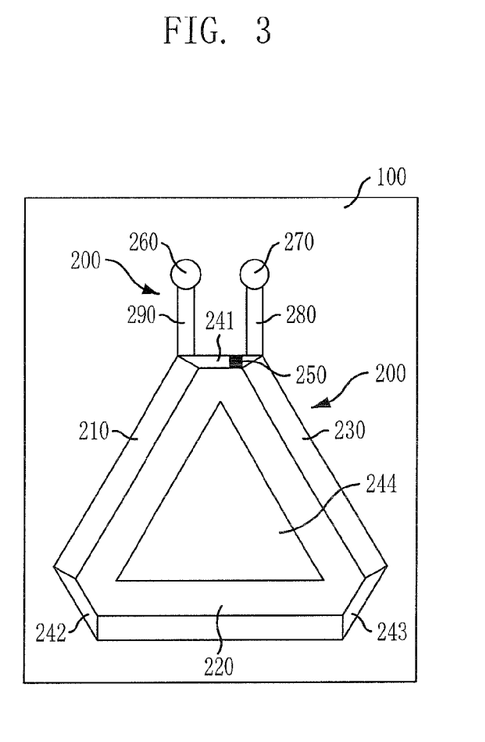
FIG. 3 is a plan view of the disposable polymer chip and a channel in accordance with an embodiment of the present invention.

FIG. 3 is a plan view of the disposable polymer chip and the channel in accordance with an embodiment of the present invention. Referring to FIG. 3, the channel 200 of the polymer chip 100 includes a denaturation channel 210, an annealing channel 230, and an extension channel 220 for three PCR temperature zones. The channels 210, 220 and 230 are connected in a loop shape by a denaturation-annealing connection channel 241, an extension-denaturation connection channel 242, and an annealing-extension connection channel 243. In addition, an inlet 260, an outlet 270, and connection channels 280 and 290 are further formed for introducing and discharging the sample. Further, a capillary stop valve 250 is installed inside the channel to charge the sample to the loop-shaped channel without interrupt due to the air layer. In order to minimize the thermal interference between the channels, an insulating hole 244 is formed by removing the center potion of the closed-curve section comprised of the loop-shaped channel.

Figure 4:
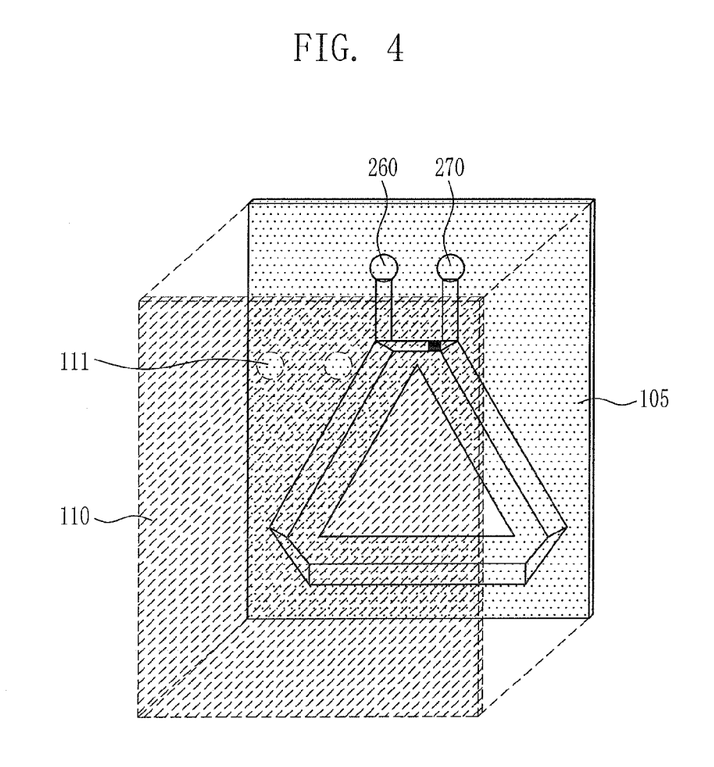
FIG. 4 illustrates a substrate attaching process for forming a channel of a disposable polymer chip in accordance with an embodiment of the present invention.

FIG. 4 illustrates a substrate attaching process for forming the channels of the disposable polymer chip in accordance with an embodiment of the present invention. Referring to FIG. 4, the channels are formed on the passage substrate 105 using an injection molding or a hot embossing. A polymer chip cover 110 includes holes 111 corresponding to the inlet 260 and the outlet 270 of the passage substrate 105. The passage substrate 105 and the polymer chip cover 110 are attached together to form the polymer chip 100. The passage substrate 105 and the chip cover 110 may be attached using a lamination process or an adhesive.

The polymer chip 100 may be formed of a material selected from the group consisting of polymethylmethacrylate (PMMA), polycarbonate (PC), cycloolefin copolymer (CC), polyamide (PA), polyethylene (PE), polypropylene (PP), polyphenylene ether (PPE), polystyrene (PS), polyoxymethylene (POM), polyetheretherketone (PEEK), polytetrafluoroethylene (PTFE), polyvinylchloride (PVC), polyvinylidene fluoride (PVDF), polybutyleneterephthalate (PBT), fluorinated ethylenepropylene (FEP), perfluoralkoxyalkane (PFA), and combination thereof.

The channel of the polymer chip 100 may be formed using various methods, e.g., a hot embossing, an injection molding, a casing, a stereolithography, a laser ablation, a rapid prototyping, a silkscreen, and a numerical control (NC) machining.

A biological, chemical and optical process may be performed on the surface of the channel of the polymer chip 100 so as to prevent components such as biological molecules in the heated fluid from being adsorbed onto the surface of the channel.

FIGS. 5A to 5E illustrate the movement of the sample in the channel of the disposable polymer chip in accordance with an embodiment of the present invention. Referring to FIGS. 5A to 5E, the capillary stop valve 250 fills the loop-shaped microchannel 200 with the sample without forming any air layer.

Figure 5A:
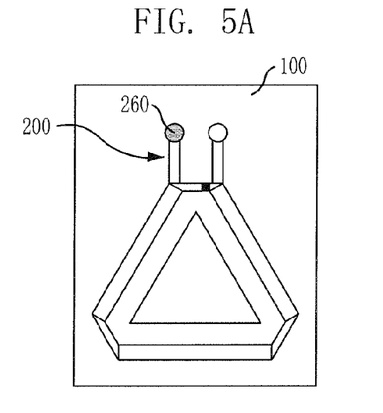
FIGS. 5A to 5E illustrate a movement of a sample in the channel of the disposable polymer chip in accordance with an embodiment of the present invention.
Figure 5B:
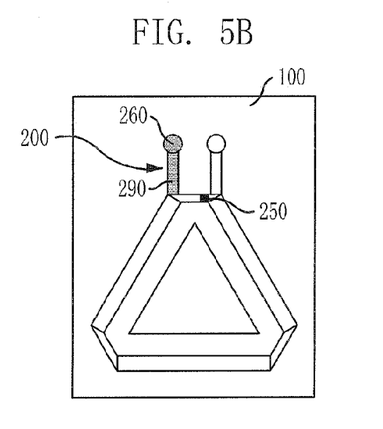
Figure 5C:
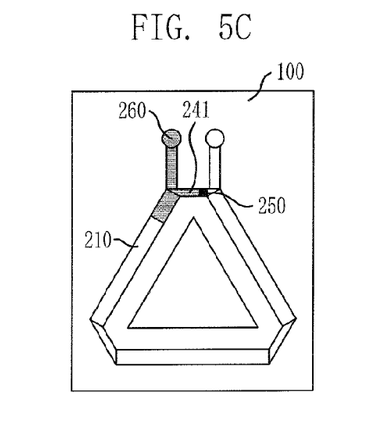
Figure 5D:
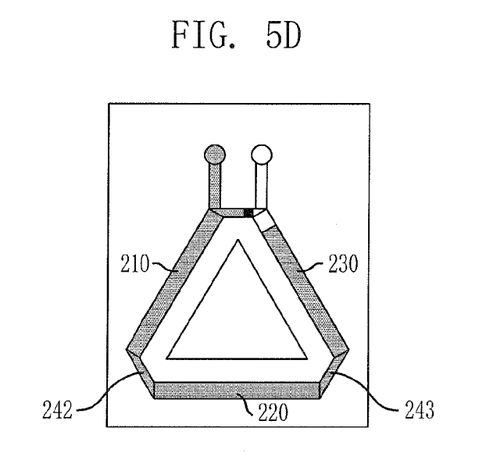
Figure 5E:
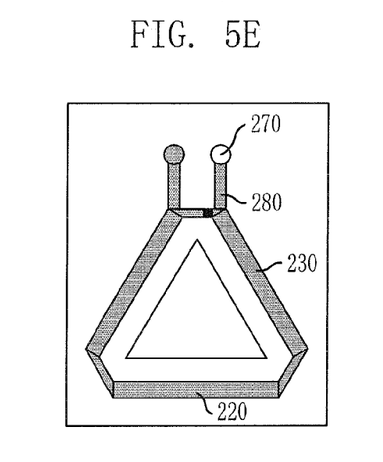

More specifically, as illustrated in FIGS. 5A to 5C, the inlet connection channel 290 is filled with the sample introduced from the inlet 260 of the channel 200, and the sample introduced from the denaturation-annealing connection channel 241 is stopped by the capillary stop valve 250 formed at the end portion. As illustrated in FIGS. 5D and 5E, the sample moved to the denaturation channel 210 moves to the annealing channel 230 and the extension channel 220 through the connection channels 242 and 243 to fill the loop-shaped microchannel 200. The sample filled in the microchannel 200 and the sample stopped by the capillary stop valve 250 move together to the outlet connection channel 280 and the outlet 270. In addition, during the sample filling process, the microchannel can be filled with the samples without interrupt due to the air layer.

Figure 6A:
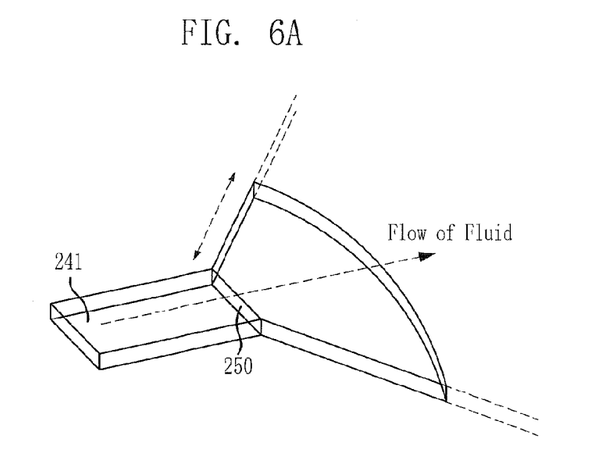
FIGS. 6A to 6C illustrate a concept of a capillary stop valve of the disposable polymer chip in accordance with an embodiment of the present invention.
Figure 6B:
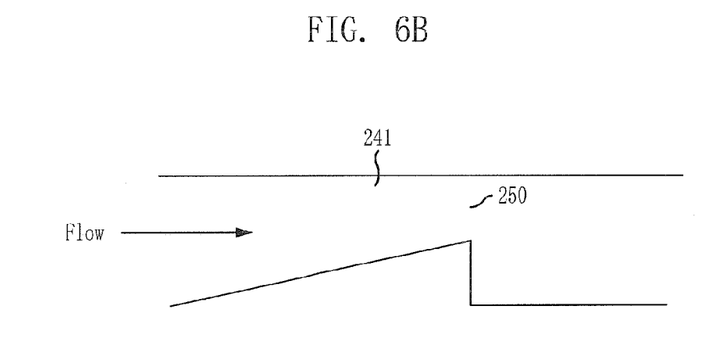
Figure 6C:
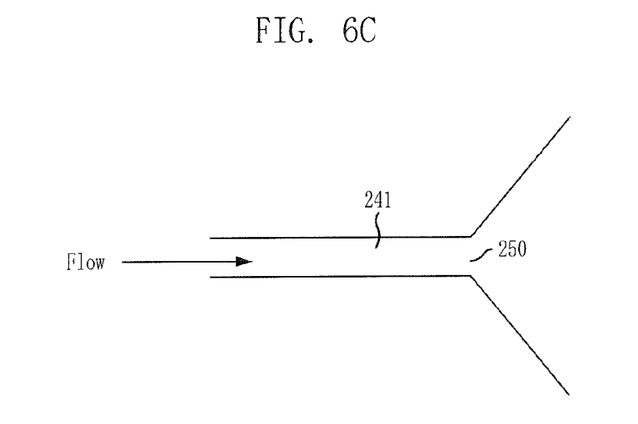

FIGS. 6A to 6C illustrate the concept of the capillary stop valve of the disposable polymer chip in accordance with an embodiment of the present invention. The capillary stop valve 250 of FIG. 6A can stop the capillary force when a stepped portion is formed in a height direction of the channel, as illustrated in FIG. 6B, and a width of the channel 241 is extended, as illustrated in FIG. 6C. Further, the sample can be more stably stopped using the two effects at the same time. It is preferable that the capillary stop valve 250 is mounted in this way.

Figure 7:
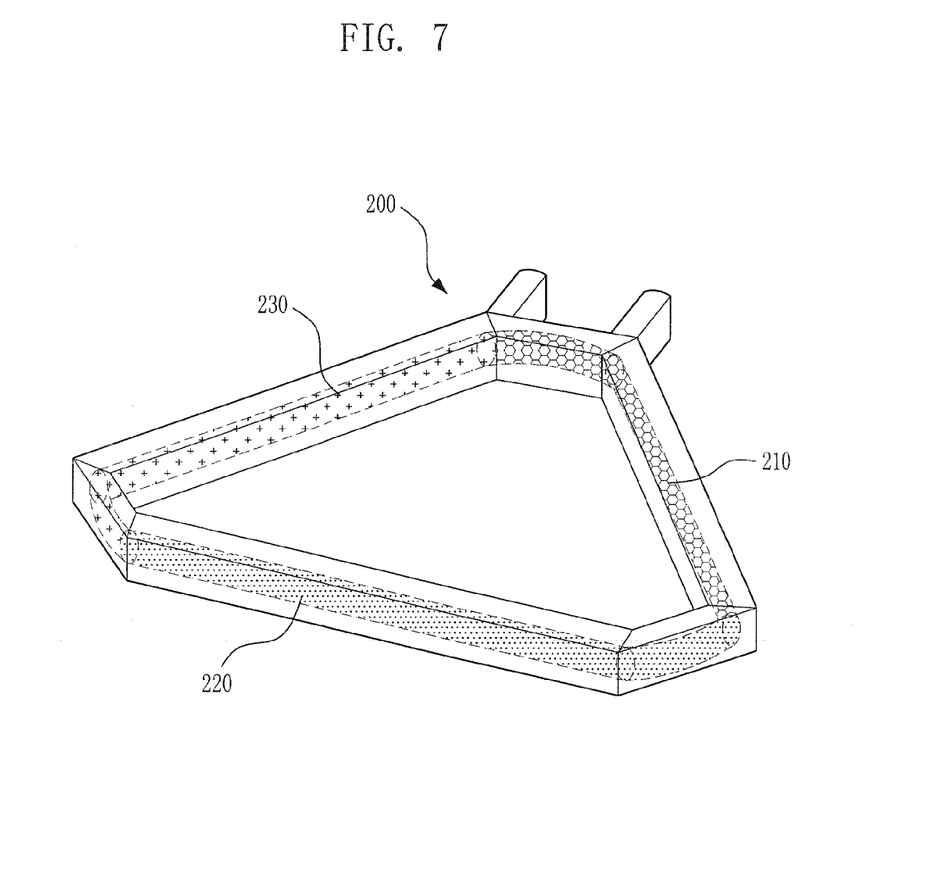
FIG. 7 illustrates a computer simulation of a sample flow inside the channel due to a natural convection of the disposable polymer chip in accordance with an embodiment of the present invention.

FIG. 7 illustrates a computer simulation of the sample flow inside the channel due to the natural convection of the disposable polymer chip in accordance with an embodiment of the present invention. As illustrated in FIG. 7, the rising flow is generated in the denaturation channel 210 due to a relatively high temperature, and the falling flow is generated in the annealing channel 230 due to a relatively low temperature. The channel 200 of the polymer chip 100 is connected in a loop shape, so that the constant flow is generated in each channel.

Figure 8A:
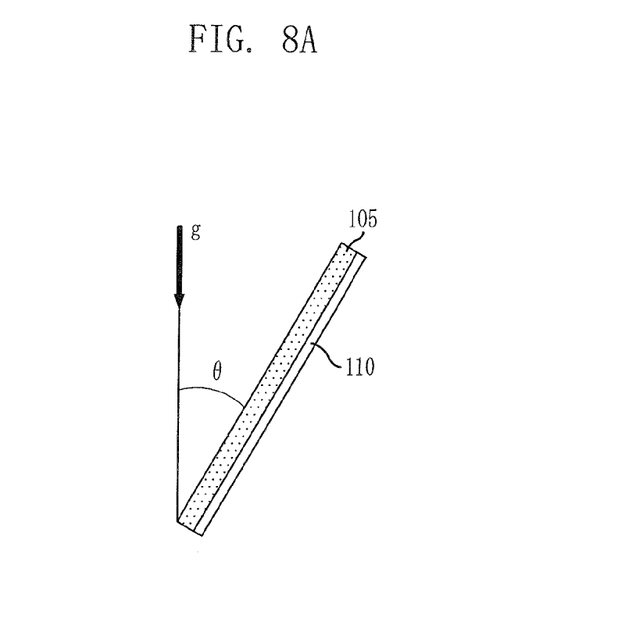
FIGS. 8A and 8B illustrate a variation of PCR time with respect to a direction of the disposable polymer chip in accordance with an embodiment of the present invention.
Figure 8B:
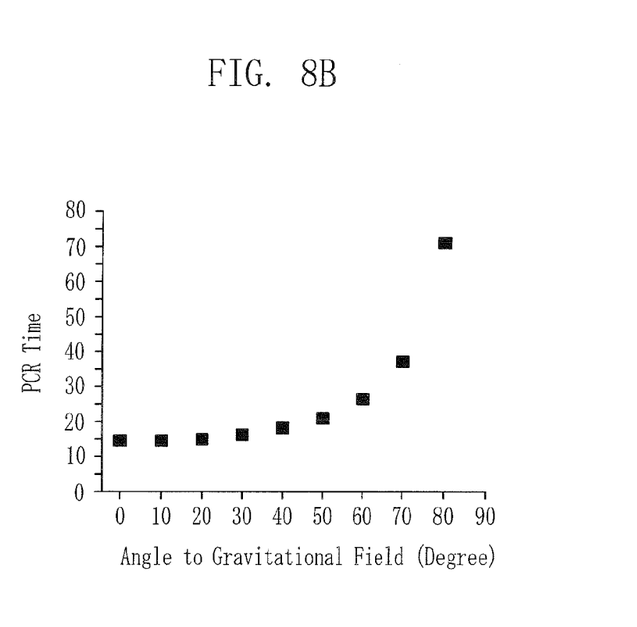

FIGS. 8A and 8B illustrate a variation of PCR time with respect to a direction of the disposable polymer chip in accordance with an embodiment of the present invention. As illustrated in FIG. 8A, the flow strength of the natural convection is determined in proportion to the magnitude of the gravitational field. Therefore, the PCR time is changed when the polymer chip 100 is inclined at a predetermined angle θ with respect to the gravitational field (g). As illustrated in FIG. 8B, the flow becomes slow as an angle between a direction of the gravitational field and a direction of the polymer chip 100 increases.

Figure 9:
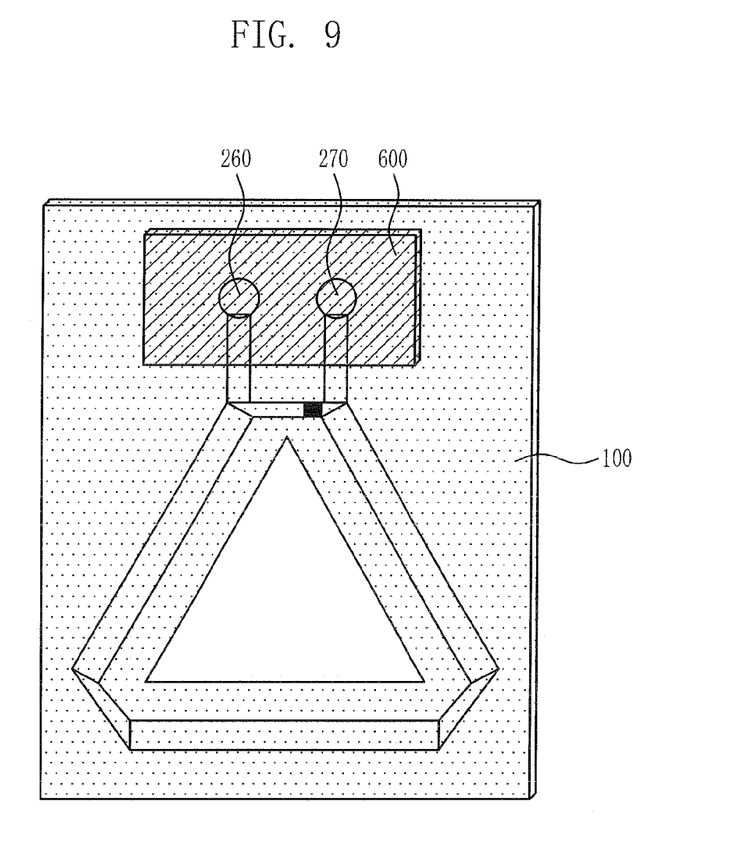
FIG. 9 is a plan view of a sealing plate for preventing evaporation of a sample in the disposable polymer chip in accordance with an embodiment of the present invention.

FIG. 9 is a plan view of a sealing plate for preventing evaporation of the sample in the disposable polymer chip in accordance with an embodiment of the present invention. Referring to FIG. 9, since the heat is applied to the sample during the PCR process, air bubbles may be generated or evaporated within the sample. To prevent this phenomenon, a sealing plate 600 is further provided. The sealing plate 600 may be attached to the inlet 260 and the outlet 270. The sealing plate 600 may be formed of an elastic material. Further, the sealing can be maintained by coating one side of the sealing plate 600 with an adhesive or mechanically pressing the sealing plate 600.

Figure 10:
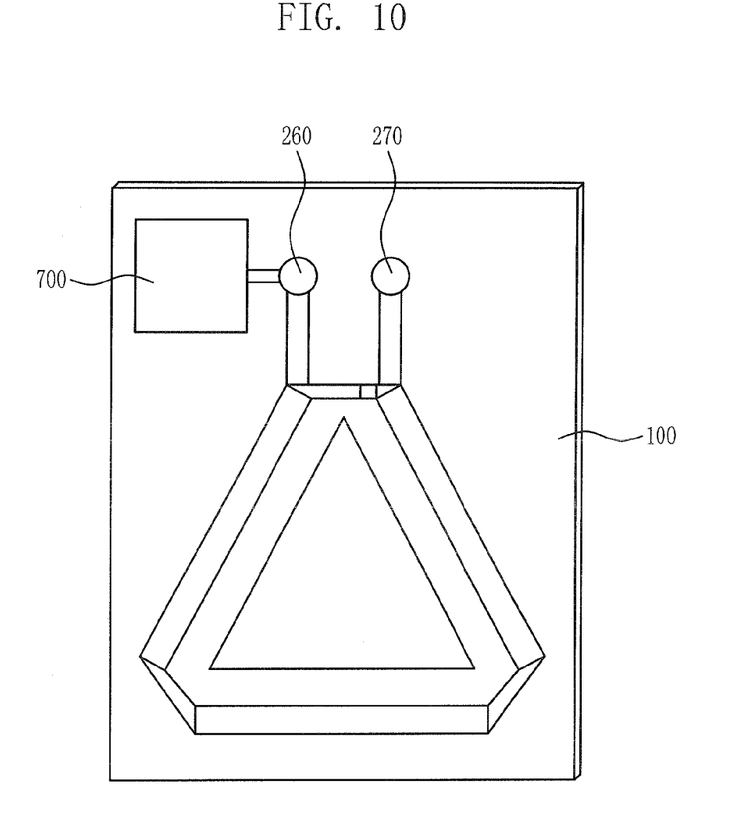
FIG. 10 is a plan view of a PCR sample pretreatment portion, which is disposed at a front end of an inlet of the disposable polymer chip, in accordance with an embodiment of the present invention.

FIG. 10 is a plan view of a PCR sample pretreatment portion, which is disposed at a front end of the inlet of the disposable polymer chip, in accordance with an embodiment of the present invention. Referring to FIG. 10, pretreatment may be required to extract DNA from the sample and purify the extracted DNA according to kinds of the PCR sample. To this end, a sample pretreatment portion 700 is provided at a front end of the inlet 260. Although the sample pretreatment portion 700 is located on the disposable polymer chip 100 as illustrated in FIG. 10, it can also be implemented with an external structure attached to the inlet 260.

The natural convection-driven PCR apparatus using the disposable polymer chip may further include a fluorescent detector for obtaining the PCR result in real time by using the polymer chip. It is apparent to those skilled in the art that fluorescent detection methods for obtaining the PCR result in real time by using the fluorescent detector can be easily implemented and the technical implementations using the fluorescent detection methods fall within the scope of the invention.

As described above, the natural convection-driven PCR apparatus using the disposable polymer chip includes the polymer chip having the channels connected in a loop shape, the heating metal member, the temperature controller, and the temperature sensors. In addition, the heating metal block is maintained at a constant temperature using the heater, the temperature controller, and the temperature sensors. The sample inside the loop-shaped microchannel is heated to a predetermined temperature using the heating metal block. The heating generates the natural convection and the sample moves along the loop due to the natural convection. The temperature for the PCR can be sequentially changed.

In accordance with the embodiments of the present invention, the loop-shaped channels are formed on the polymer chip, and the heating metal members maintained at different temperatures contact the channels. The flow due to the natural convection is generated in the channels. Therefore, the temperature of the sample is periodically changed. Since the polymer substrate is used, mass production can be possible. The portability of the PCR apparatus can be improved because the simple temperature control is required instead of additional flow control. Since the polymer chip is fabricated in a microchannel type, the sample flows smoothly and the accurate temperature change of the sample can be achieved, thereby minimizing the interference between the samples. The sample can be fully filled inside the loop-shaped microchannel due to only the capillary flow without any air layer and thus the samples can move smoothly.

The natural convection-driven PCR methods using the disposable polymer chip in accordance with the embodiments of the present invention can be realized as programs and stored in a computer-readable recording medium that can execute the programs. Examples of the computer-readable recording medium include CD-ROM, RAM, ROM, floppy disks, hard disks, magneto-optical disks and the like.

While the present invention has been described with respect to the specific embodiments, it will be apparent to those skilled in the art that various changes and modifications may be made without departing from the spirit and scope of the invention as defined in the following claims.

What is claimed is:

1. A natural convection-driven polymerase chain reaction (PCR) apparatus using a disposable polymer chip, comprising:
    a polymer chip having a plurality of channels connected together to form a loop-shaped microchannel, a sample being filled inside the channels;
    a plurality of heating metal members contacting the loop-shaped microchannel of the polymer chip and transferring heat;
    a temperature controller connected to the heating metal members to maintain the heating metal members at different temperatures;
    a plurality of heaters connected to the heating metal members and the temperature controller to supply heat to the heating metal members; and
    a plurality of temperature sensors connected to the heating metal members and the temperature controller, wherein the PCR apparatus is configured such that the sample is driven around the loop only by the natural convection generated by the heat supplied to the heating metal members;
    the loop-shaped microchannel includes a capillary stop valve disposed adjacent an outlet connection channel on a side facing an inlet connection channel to fill the channels with the sample without an air layer by stopping part of the sample introduced from the inlet connection channel by the capillary stop valve and allowing the sample filled in the microchannel and the sample stopped by the capillary stop valve to move together to the outlet connection channel; and
    the PCR apparatus periodically changes temperature of the sample to make a natural convection-driven flow in the loop-shaped microchannel by forming the loop-shaped microchannel on the disposable polymer chip and contacting the heating metal members maintained at the different temperatures with the channels.

2. The natural convection-driven PCR apparatus of claim 1, wherein the loop-shaped microchannel further includes:
    an inlet through which the sample is introduced;
    a plurality of channels;
    a connection channel connecting the channels and through which the sample flows; and
    an outlet through which the sample is discharged.

3. The natural convection-driven PCR apparatus of claim 1, wherein the channels include a denaturation channel, an annealing channel, and an extension channel.

4. The natural convection-driven PCR apparatus of claim 1, wherein the polymer chip is formed by attaching a polymer film to a passage substrate having the channels formed using an injection molding or a hot embossing.

5. The natural convection-driven PCR apparatus of claim 4, wherein the passage substrate and the polymer film are attached using a lamination process or an adhesive.

6. The natural convection-driven PCR apparatus of claim 1, wherein surfaces of the channels of the polymer chip are processed biologically, chemically and optically, thereby preventing biological molecule components in the heated fluid from being adsorbed onto the surfaces of the channels.

7. The natural convection-driven PCR apparatus of claim 1, wherein the heating metal member includes:
    a heating metal block connected to the heater to transfer heat generated from the heater;
    a heating metal pin protruding from the heating metal block to transfer heat generated from the heating metal block; and
    a heating metal contact block having one side protruding from the heating metal pin and contacting the channel of the polymer chip.

8. The natural convection-driven PCR apparatus of claim 7, wherein the heating metal block, the heating metal pin, and the heating metal contact block are integrated such that the heating metal member is formed in a multiple slot shape, whereby a plurality of polymer chips are inserted thereinto.

9. The natural convection-driven PCR apparatus of claim 7, wherein the heating metal block is maintained at a constant temperature by the heater, the temperature controller, and the temperature sensors, and the sample inside the loop-shaped microchannel is heated to a constant temperature by the heating metal block, such that the sample flows along the loop and the temperature sequentially changes.

10. The natural convection-driven PCR apparatus of claim 1, wherein the heater is one of a film heater, a ceramic heater, and a rod heater.

11. The natural convection-driven PCR apparatus of claim 1, wherein the heating metal members contact both sides of the loop microchannel of the polymer chip and transfer generated heat to the loop microchannel.

12. The natural convection-driven PCR apparatus of claim 1, wherein the polymer chip is inclined at a predetermined angle with respect to a gravitational field to control a natural convection-driven PCR time.

13. The natural convection-driven PCR apparatus of claim 1, wherein the polymer chip further includes a sealing plate for sealing an inlet and an outlet from outside air so as to prevent air bubbles from being generated or evaporated in the sample during the PCR process.

14. The natural convection-driven PCR apparatus of claim 1, wherein the polymer chip further includes a pretreatment portion provided at a front end of an inlet of the polymer chip to perform pretreatment onto a PCR sample.

15. The natural convection-driven PCR apparatus of claim 1, wherein the polymer chip is formed of a material selected from the group consisting of polymethylmethacrylate (PMMA), polycarbonate (PC), cycloolefin copolymer (CC), polyamide (PA), polyethylene (PE), polypropylene (PP), polyphenylene ether (PPE), polystyrene (PS), polyoxymethylene (POM), polyetheretherketone (PEEK), polytetrafluoroethylene (PTFE), polyvinylchloride (PVC), polyvinylidene fluoride (PVDF), polybutyleneterephthalate (PBT), fluorinated ethylenepropylene (FEP), perfluoralkoxyalkane (PFA), and combination thereof.

16. A natural convection-driven polymerase chain reaction (PCR) method using a natural convection-driven PCR apparatus employing a disposable polymer chip, wherein
the PCR apparatus includes:
- a polymer chip having a plurality of channels connected together to form a loop-shaped microchannel, a sample being filled inside the channels,
- a plurality of heating metal members contacting the loop-shaped microchannel of the polymer chip and transferring heat,
- a temperature controller connected to the heating metal members to maintain the heating metal members at different temperatures,
- a plurality of heaters connected to the heating metal members and the temperature controller to supply heat to the heating metal members, and
- a plurality of temperature sensors connected to the heating metal members and the temperature controller, wherein
- the PCR apparatus is configured such that the sample is driven around the loop only by the natural convection generated by the heat supplied to the heating metal members;
- the loop-shaped microchannel includes a capillary stop valve disposed adjacent an outlet connection channel on a side facing an inlet connection channel to fill the channels with the sample without an air layer by stopping part of the sample introduced from the inlet connection channel by the capillary stop valve and allowing the sample filled in the microchannel and the sample stopped by the capillary stop valve to move together to the outlet connection channel; and
- the PCR apparatus periodically changes temperature of the sample to make a natural convection-driven flow in the loop-shaped microchannel by forming the loop-shaped microchannel on the disposable polymer chip and contacting the heating metal members maintained the different temperatures with the channels, the natural convection-driven PCR method comprising:
a) maintaining each of the plurality of heating metal members at a respective constant temperature using respective ones of the plurality of heaters, temperature controllers, and temperature sensors;
b) heating the sample in the respective channel to the respective constant temperature by contacting the respective heating metal member with the polymer chip;
c) generating the natural convection due to the heat supplied to the plurality of heating metal members; and
d) sequentially changing the temperature of the sample only by moving the sample along the loop due to the natural convection.

* * * * *